United States Patent
Crotts et al.

(10) Patent No.: US 7,316,819 B2
(45) Date of Patent: Jan. 8, 2008

(54) ORAL PEPTIDE PHARMACEUTICAL DOSAGE FORM AND METHOD OF PRODUCTION

(75) Inventors: George Crotts, Kintnersvill, PA (US); Isaac Ghebre-Sellassie, Morris Plains, NJ (US); Ashlesh Sheth, Randolph, NJ (US)

(73) Assignee: Unigene Laboratories, Inc., Fairfield, NJ (US)

( * ) Notice: Subject to any disclaimer, the term of this patent is extended or adjusted under 35 U.S.C. 154(b) by 247 days.

(21) Appl. No.: 10/094,306

(22) Filed: Mar. 7, 2002

(65) Prior Publication Data

US 2003/0017203 A1    Jan. 23, 2003

Related U.S. Application Data

(60) Provisional application No. 60/274,317, filed on Mar. 8, 2001.

(51) Int. Cl.
*A61K 9/20* (2006.01)
*A61K 9/16* (2006.01)

(52) U.S. Cl. .............. 424/464; 424/465; 424/490; 424/491

(58) Field of Classification Search .............. 424/464, 424/451, 490
See application file for complete search history.

(56) References Cited

U.S. PATENT DOCUMENTS

| 5,312,899 | A |   | 5/1994 | Schiller .................. 514/18 |
| 5,602,100 | A |   | 2/1997 | Brown et al. ............. 514/18 |
| 5,614,219 | A |   | 3/1997 | Wunderlich et al. ....... 424/472 |
| 5,912,014 | A |   | 6/1999 | Stern et al. ............. 424/474 |
| 6,039,975 | A | * | 3/2000 | Shah et al. ............. 424/473 |
| 6,086,918 | A | * | 7/2000 | Stern et al. ............. 424/474 |
| 6,309,666 | B1 | * | 10/2001 | Hatano et al. ............ 424/463 |

FOREIGN PATENT DOCUMENTS

| WO | WO 95/34295 | 12/1995 |
| WO | WO 97/33531 | 9/1997 |
| WO | WO9733531   | 9/1997 |
| WO | WO 99/64449 | 12/1999 |
| WO | WO 01/27154 | 4/2001 |

OTHER PUBLICATIONS

Remington's Pharmaceutical Sciences, 18th edition, pp. 1319, 1634-38 (1990).*
Search Report issued for corresponding International Application No. PCT/US02/07197.
European Search Report dated Aug. 30, 2005.
International Search Report dated Oct. 26, 2005.
Takahashi, Ken-Ichiro et al.: "Production of Bioactive Salmon Calcitonin From the Nonendocrine Cell Lines COS-7 and CHO", PEPTIDES, vol. 18, No. 3, pp. 439-444, 1997, XP002341274 ISSN: 0196-9781/97.
Lu, Jun et al.: "TAP-Independent Presentation 1 of CTL Epitopes by Trojan Antigens", Journal of Immunology, vol. 166, No. 12, pp. 7063-7071, Jun. 15, 2001, XP002341273, ISSN: 0022-1767/01.

* cited by examiner

*Primary Examiner*—Isis Ghali
(74) *Attorney, Agent, or Firm*—Ostrolenk, Faber, Gerb & Soffen, LLP

(57) ABSTRACT

A pharmaceutical composition for oral delivery of a peptide is in the form of a lamination having at least two layers. The first layer of the lamination includes at least one pharmaceutically acceptable pH-lowering agent. The second layer includes a therapeutically effective amount of the peptide. The composition also includes at least one absorption enhancer effective to promote bioavailability of the peptide, which is preferably in the second layer, and an enteric coating surrounding the lamination. In a preferred dosage form of a tablet, a water-soluble coating is applied between the lamination and enteric coating which substantially prevents contact between the pH-lowering agent and the enteric coating. In a preferred embodiment, the peptide is salmon calcitonin, the pH-lowering agent is citric acid, and the absorption enhancer is lauroyl l-carnitine.

30 Claims, No Drawings

ORAL PEPTIDE PHARMACEUTICAL DOSAGE FORM AND METHOD OF PRODUCTION

This application claims priority benefit of provisional application Ser. No. 60/274,317 filed Mar. 8, 2001.

FIELD OF THE INVENTION

The present invention relates to oral peptide pharmaceutical dosage forms, to methods of enhancing the bioavailability of orally administered peptides, and to methods of production of tableted dosage forms useful for the treatment of disorders in humans by orally administering a peptide in accordance with the invention.

BACKGROUND OF THE INVENTION

Salmon calcitonin is a peptide hormone that decreases uptake of calcium from bone. When used to treat bone-related diseases and calcium disorders (such as osteoporosis, Paget's disease, hypercalcemia of malignancy, and the like), it has the effect of helping maintain bone density. Many types of calcitonin have been isolated, such as human calcitonin, salmon calcitonin, eel calcitonin, elkatonin, porcine calcitonin, and chicken calcitonin. There is significant structural non-homology among the various calcitonin types. For example, there is 50% identity between the amino acids making up human calcitonin and those making up salmon calcitonin.

Salmon calcitonin used in the prior art has usually been administered by injection or by nasal administration. However, these modes of administering the calcitonin are significantly less convenient than oral administration and involve more patient discomfort. Often this inconvenience or discomfort results in substantial patient noncompliance with a treatment regimen. However, the prior art is not believed to have reported an ability to achieve reproducible blood levels of peptides such as salmon calcitonin when administered orally. This is believed to be because these peptides lack sufficient stability in the gastrointestinal tract, and tend to be poorly transported through intestinal walls into the blood.

Proteolytic enzymes of both the stomach and intestines may degrade salmon calcitonin, rendering it inactive before the calcitonin can be absorbed into the bloodstream. Any salmon calcitonin that survives proteolytic degradation by proteases of the stomach (typically having acidic pH optima) is later confronted with proteases of the small intestine and enzymes secreted by the pancreas (typically having neutral to basic pH optima). Other difficulties arising from the oral administration of salmon calcitonin involve the relatively large size of the molecule, and the charge distribution it carries. This may make it more difficult for salmon calcitonin to penetrate the mucus along intestinal walls or to cross the intestinal brush border membrane into the blood. These additional problems may further contribute to the limited bioavailability of salmon calcitonin.

U.S. Pat. No. 5,912,014 (the '014 patent) to Stern et al. describes a therapeutically effective oral pharmaceutical composition for delivering salmon calcitonin into the small intestine. According to that patent, it is believed that protecting the salmon calcitonin with an enteric coating can reduce the likelihood of proteolytic degradation of the salmon calcitonin in the stomach. Although the patent describes salmon calcitonin administration in a tablet form, the patent does not disclose a commercially viable dosage form comprising a peptide generally, nor does it describe a method of making such a dosage form. For example, during the compression phase of a composition prepared according to the '014 patent, it was found that some material would irreversibly stick to the tooling surface. Moreover, a monolayer tablet prototype exhibited poor stability when stored at ambient conditions. The '014 patent also does not describe solutions to the problems that arise in combining peptides, surfactants, and pH-lowering agents in a single enteric coated dosage form for production at a commercial scale.

Notwithstanding the foregoing, there is a need in the art for a commercially viable dosage form that maintains peptide stability in the presence of pH-lowering agents.

SUMMARY OF THE INVENTION

In one aspect, the invention provides a pharmaceutical composition for oral delivery of a peptide. The composition comprises a lamination having at least two layers. The first layer comprises at least one pharmaceutically acceptable pH-lowering agent. The second layer comprises a therapeutically effective amount of a peptide. The composition also includes at least one absorption enhancer effective to promote bioavailability of the peptide, which is preferably in the second layer. The composition also includes an enteric coating surrounding the lamination.

A second aspect of the invention provides a method for enhancing the bioavailability of a peptide delivered orally. The method comprises selectively releasing a peptide, together with at least one pH-lowering agent and at least one absorption enhancer, into a patient's intestine following passage of the peptide, pH-lowering agent, and absorption enhancer through a patient's mouth and stomach under protection of an enteric coating and a water-soluble coating. The enteric coating substantially prevents contact between stomach proteases and the peptide, while the water-soluble coating further substantially prevents contact between the pH-lowering agent and the enteric coating.

A third aspect of the invention provides a tableted dosage form for the delivery of a peptide and the method of making the same. The dosage form comprises a lamination having a first layer comprising at least one pharmaceutically acceptable pH-lowering agent and a second layer comprising a therapeutically effective amount of a peptide. The dosage form also includes at least one absorption enhancer effective to promote bioavailability of the peptide, a water-soluble coating formed over the lamination, and an enteric coating formed over the water-soluble coating. As detailed below, the water-soluble coating substantially prevents contact between the pH-lowering agent and the enteric coating, thereby substantially preventing inhibition of the dissolution of the enteric coating by the pH-reducing agent.

According to a method for making a dosage form, a pH-lowering agent is granulated to form a first layer material. A peptide and at least one absorption enhancer are combined to form a second layer material. Then, the first and second layer materials are formed into a lamination having at least two layers. The method also includes coating the lamination with a water-soluble coating to form a coated lamination and then forming an enteric coating over the coated lamination.

It is to be understood that both the foregoing general description and the following detailed description are exemplary, but are not restrictive, of the invention.

DETAILED DESCRIPTION OF THE INVENTION

In accordance with the invention, patients in need of treatment with a peptide, such as calcitonin or salmon calcitonin, are provided with an oral dosage form containing the peptide in a tablet of an ordinary size in the pharmaceutical industry. In accordance with this invention, the dosage form or composition includes a lamination having at least two layers. As used herein, the term "lamination" shall have its conventional meaning as something which is composed of layers of firmly united material, but which involves little interaction between the layers. The first layer comprises at least one pharmaceutically acceptable pH-lowering agent and the second layer comprises a therapeutically effective amount of a peptide. The composition also includes at least one absorption enhancer effective to promote bioavailability of the peptide, and an enteric coating surrounding the lamination. The composition may be in the form of a capsule or tablet, and preferably as in the form of a tablet, in which case a water-soluble coating is applied over the lamination, between the lamination and the enteric coating. For the reasons described below, when the peptide is salmon calcitonin and the pH lowering agent is citric acid, it is preferable to have the absorption enhancer, such as lauroyl l-carnitine, incorporated into the second layer. The dosages and frequency of administering the products are performed in manners well known in the art.

Patients who may benefit are any who suffer from disorders or diseases that are treatable by administration of a peptide. The invention may be used, for example, to treat osteoporosis, Paget's disease, hypercalcemia, and other diseases treatable by administration of a peptide.

Salmon calcitonin is a preferred peptide for use in accordance with the invention because it has been widely characterized, its properties are well known, it provides a number of advantages over human calcitonin, and it is used as a pharmaceutical agent for human patients. Among the advantages provided by utilizing salmon calcitonin instead of human calcitonin for the treatment of human osteoporosis are increased potency, analgesia, and increased half-life.

The pharmaceutical composition of the invention overcomes a series of different and unrelated natural barriers to bioavailability. Various components of the pharmaceutical composition act to overcome different barriers by mechanisms appropriate to each, and result in synergistic effects on the bioavailability of the peptide. However, as discussed below, inherent physical and chemical properties of peptides, enteric coatings and pH-lowering agents, without more, are also counterproductive in boosting bioavailability and enhancing stability of the dosage form when combined together.

The peptide of the invention is typically administered orally. In accordance with the invention, proteolytic degradation of the peptides by stomach proteases (most of which are active in the acid pH range) and intestinal or pancreatic proteases (most of which are active in the neutral to basic pH range) is reduced. Furthermore, solubility enhancers or surfactants aid passage of the peptide active agent through the intestinal epithelial barrier.

Without intending to be bound by theory, it appears that, in accordance with the present invention, the peptide is transported through the stomach under the protection of an enteric coating or other appropriate vehicle for substantially preventing contact between the peptide and any stomach proteases capable of degrading the peptide. Accordingly, it is desirable to select a material for the enteric coating and an appropriate thickness of the coating such that the coating protects the pharmaceutical composition for a sufficient time to allow the dosage form to no longer be exposed to stomach proteases. Once the pharmaceutical composition of the invention passes through the stomach and enters the intestinal region where basic to neutral pH predominates, and where proteases tend to have basic to neutral pH optima, the composition releases the peptide and acid (in close proximity to each other).

It is believed the acid lowers the local intestinal pH, where the active agent has been released to levels below the optimal range for many intestinal proteases. This decrease in pH reduces the proteolytic activity of the intestinal proteases, thus affording protection to the peptide from potential degradation. In other words, the activity of these proteases is diminished by the temporarily acidic environment provided by pH lowering agent. It is preferred that sufficient acid be provided that local intestinal pH is lowered temporarily to 5.5 or below, especially a range between about 4.0 and 5.5. The sodium bicarbonate test described below (and in U.S. Pat. No. 5,912,014, incorporated herein by reference) is indicative of the required acid amount. Preferably, conditions of reduced intestinal pH persist for a time period sufficient to protect the peptide agent from proteolytic degradation until at least some (and preferably most or all) of the peptide agent has had an opportunity to cross the intestinal wall into the bloodstream.

The absorption enhancer, which may be a solubility enhancer and/or transport enhancer (as described in the '014 patent), aids transport of the peptide agent from the intestine to the blood, and may speed the process so that it better occurs during the time period of reduced intestinal pH and reduced intestinal proteolytic activity. Many surface active agents may act as both solubility enhancers and uptake enhancers. Again, without intending to be bound by theory, it is believed that enhancing solubility provides (1) a more simultaneous release of the active components of the invention into the aqueous portion of the intestine, and (2) better solubility of the peptide in, and transport through, a mucous layer along the intestinal walls. Once the peptide reaches the intestinal walls, an uptake enhancer provides better transport through the brush border membrane of the intestine into the blood, via either transcellular or paracellular transport. As discussed in more detail below, many preferred compounds may provide both functions. In those instances, preferred embodiments utilizing both of these functions may do so by adding only one additional compound to the pharmaceutical composition, although it is not necessary that the absorption enhancer provide both of these functions. It should be pointed out that the term "absorption enhancer" as used herein may function either as a solubility enhancer, a transport enhancer, or both. In particular, with respect to lauroyl l-carnitine, it appears that this absorption enhancer functions as at least a solubility enhancer.

Each of the preferred ingredients of the pharmaceutical composition of the invention is separately discussed below. Combinations of multiple pH-lowering agents or surfactants can be used as well as using just a single pH-lowering agent and single surfactant. Some preferred combinations are discussed below.

The Peptide

The peptide is preferably present in an amount that is therapeutically effective in a typical dosage form provided commercially. This exact amount will vary depending on the peptide use, its solubility, the disease or illness being treated, bioavailability, as well as many other factors well known in the art. When the peptide is salmon calcitonin, it has been found that the peptide may be present in an amount of from about 0.02 to 0.2% by weight relative to the total weight of the overall pharmaceutical composition (exclusive of enteric coating). Although calcitonin is the typical peptide used in the present invention, with salmon calcitonin preferred, other peptides for use in the present invention include the peptides described in the '014 patent.

Peptide precursors may be made by either chemical or recombinant syntheses known in the art. However, the latter is believed significantly more cost effective. The production of recombinant salmon calcitonin (rsCT) may proceed, for example, by producing glycine-extended salmon calcitonin precursor in *E. coli* as a soluble fusion protein with glutathione-S-transferase, as described in the '014 patent.

The pH-Lowering Agent

The total amount of the pH lowering compound to be administered with each administration of peptide should preferably be an amount which, when it is released into the intestine, is sufficient to lower the local intestinal pH substantially below the pH optima for proteases found in the local area of the intestine. The quantity required will necessarily vary with several factors including the type of compound used and the equivalents of protons provided by a given compound in practice. The typical amount required to provide good bioavailability for the administered peptide is an amount which, when added to a solution of 10 milliliters of 0.1 M sodium bicarbonate, lowers the pH of that sodium bicarbonate solution to no higher than 5.5, and preferably to between 4.0 and 5.5.

The pH-lowering agent of the invention may be any pharmaceutically acceptable compound that is not toxic in the gastrointestinal tract and is capable of either delivering hydrogen ions (a traditional acid) or of inducing higher hydrogen ion content from the local environment. It may also be any combination of such compounds. Examples of compounds are well known in the art, as described in the '014 patent. In the present invention, citric acid is preferred.

The Absorption Enhancer

One or more absorption enhancers (also referred to herein as surfactants) are preferably present in a quantity that shows some improvement in promoting the bioavailability of the peptide. Typically, this amount may constitute from 0.1 to 20.0% by weight, relative to the overall weight of the pharmaceutical composition (exclusive of the enteric coating). Preferred absorption enhancers are surface active agents which act both as solubility enhancers or uptake enhancers or both. As mentioned above, "solubility enhancers" improve the ability of the active components of the invention to be solubilized in either the aqueous environment into which they are originally released or into the lipophilic environment of the mucous layer lining the intestinal walls, or both. "Uptake enhancers" (which are frequently the same surface active agents used as solubility enhancers) are those which facilitate the ease by which peptide agents cross the intestinal wall.

One or more absorption enhancers may perform one function only (e.g., solubility), or one or more absorption enhancers may perform the other function only (e.g., uptake), within the scope of the invention. It is also possible to have a mixture of several compounds some of which provide improved solubility, some of which provide improved uptake and/or some of which perform both, as described in U.S. Pat. No. 5,912,014. Without intending to be bound by theory, it is believed that uptake enhancers may act by (1) increasing disorder of the hydrophobic region of the membrane exterior of intestinal cells, allowing for increased transcellular transport; (2) leaching membrane proteins resulting in increased transcellular transport; or (3) widening pore radius between cells for increased paracellular transport.

When surface active agents are used as the absorption enhancers, it is preferred that they be free flowing powders for facilitating mixing. However, because of inherent characteristics of peptides (e.g., isoelectric point, molecular weight, amino acid composition, etc.) certain surface active agents are preferred. Indeed, some can undesirably interact with the charged portions of the peptide and prevent its absorption, thus undesirably resulting in decreased bioavailability. It is well within the skill of one in the art to determine which surface active agents are most suitable for increasing the bioavailability of the peptide. For example, when the peptide comprises salmon calcitonin, the surface active agent used as an absorption enhancer should be selected from the group consisting of (i) anionic surface active agents that are cholesterol derivatives (e.g., bile acids), (ii) cationic surface agents (e.g., acyl-carnitines, phospholipids and the like), (iii) nonionic surface active agents, and (iv) mixtures of anionic surface active agents (especially those having linear hydrocarbon regions) together with negative charge neutralizers for salmon calcitonin.

When the peptide is salmon calcitonin, negative charge neutralizers include but are not limited to acyl-carnitines, cetyl pyridinium chloride, and the like. Preferably, the charge neutralizer is lauroyl l-carnitine. It is also preferred that the absorption enhancer be soluble at acid pH, particularly in the pH=3.0 to 5.0 range. When a single absorption enhancer is used alone, it is preferred that it be a cationic surface active agent. It is the intent of these preferences to avoid interactions with the peptide that interfere with absorption of peptide into the blood.

Other Optional Ingredients

All pharmaceutical compositions of the invention may optionally also include common pharmaceutical binders such as povidone, diluents, glidants, fillers such as microcrystalline cellulose, lubricants such as magnesium stearate, disintegrants such as croscarmellose sodium, preservatives, colorants and the like in their usual known sizes and amounts. In some embodiments, peptides that may act as substrates for intestinal proteases are added (preferably from 0.2 to 10.0% by weight relative to the weight of the overall pharmaceutical composition (exclusive of enteric coating)).

The Enteric Coating

Any enteric coating that protects the peptide from stomach proteases and which releases active components of the invention in the intestine is suitable. The enteric coating functions by providing a coating that does not dissolve in low pH environments, such as the stomach. Many enteric coatings are known in the art, and are useful in accordance with the invention. Examples include cellulose acetate phthalate, hydroxypropylmethylethylcellulose succinate, hydroxypropylmethylcellulose phthalate, polyvinyl acetate phthalate, and methacrylic acid-methyl methacrylate copolymer.

It is very desirable that all of the active components be released from the dosage form, and solubilized in the intestinal environment as simultaneously as possible. It is preferred that the dosage form release the active components in the small intestine. To this end, it is desirable to use an enteric coating material. Preferably, the enteric coating adds no more than 20% to the weight of the remainder of pharmaceutical composition (exclusive of enteric coating). More preferably, it adds from 3 to 15% to the weight of the uncoated composition.

The Water-Soluble Coating

Any water-soluble coating that substantially prevents contact between the pH-lowering agent and the enteric coating is suitable. Many water-soluble coatings are known in the art, and are useful in accordance with the invention. Examples include hydroxypropylnethylcellulose, hydroxypropylcellulose and methylcellulose.

As described above, it is very desirable that all of the active components be released from the dosage form and solubilized in the intestinal environment as simultaneously as possible. However, the pH-lowering agent typically inhibits the dissolution of the enteric coating by lowering the local pH. To solve this problem, in one embodiment, the inventors have provided a water-soluble coating positioned between the dosage form and the enteric coating, thereby substantially preventing contact between the pH-lowering agent and the enteric coating.

Preferably, the water-soluble coating adds no more than 20% to the weight of the remainder of pharmaceutical composition (exclusive of water-soluble coating). Typically, the water-soluble coating adds no more than 0.5 to 10% to the weight of the pharmaceutical composition. More preferably, it adds from 0.5 to 5% to the weight of the uncoated composition.

The Dosage Form and Manufacture Thereof

The dosage form of the present invention typically comprises a tablet comprising a lamination of at least two layers. The primary component of the first layer is typically the pH-lowering agent described above. The primary components of the second layer are typically the peptide and, optionally, the absorption enhancer. When combined in the manner described below, the constituents form a tablet having at least two layers. Although a two layer tablet is preferred due to its relative ease of manufacture, it is also possible to have three or more layers wherein the second layer is substantially comprised of the peptide and the third layer comprises the surfactant.

The first layer is manufactured by granulating at least one pH-lowering agent to form a first layer material. While citric acid is the preferred pH-lowering agent, citric acid alone does not exhibit the required compressibility characteristics. Therefore, during and after the granulation, other materials may be added to the pH-lowering agent to improve its mechanical properties. Specifically, during granulation in a fluidized bed, filler materials such as microcrystalline cellulose and a povidone binder may be added in amounts well known in the art. Next, the resultant granulation is dried and optionally sized in a mill in any manner well understood to those of ordinary skill in the art. Additionally, the granulation may be combined with glidants and lubricants such as talc and magnesium stearate, as described above, to further improve compressibility and flowability of the granulation, thereby forming the first layer material.

The second layer material is formed by combining a peptide and at least one absorption enhancer (i.e., a surfactant). The second layer also may be manufactured in a fluidized bed. Because the peptide exhibits relatively high biological activity in small quantities, the second layer is produced by spraying the peptide and a binding agent, such as povidone, upon a surfactant or a mixture of at least one excipient and the surfactant. As described above, the surfactant is typically an acyl carnitine, with lauroyl l-carnitine preferred in the present invention. The optional excipient typically comprises an amount of a filler, such as microcrystalline cellulose, sufficient to provide proper adhesion between the layers, as understood by one of ordinary skill in the art. The resultant granulation is then dried and optionally sized in a mill in any manner well understood to those of ordinary skill in the art. Finally, the granulation is optionally transferred to a blender where the granulation is optionally blended with a disintegrant such as croscarmellose sodium or one or more other suitable disintegrants in amounts up to about 10.0% of the weight of the granulation, with about 2.0% by weight preferred. Although optional, without the disintegrants, bioavailability of the peptide may be compromised because complete release of the peptide may not be effected at the same time as the pH-lowering agent.

Other lubricants and additives such as magnesium stearate and stearic acid as well as other excipients such as colloidal silicon dioxide and povidone may also be added to improve the properties of the second layer material in a manner known in the art.

Next, a portion of the first layer material is fed to a standard two-layer tableting press and filled into a die or mold. The first layer material is then partially compressed to create a first layer. The partial compression is typically necessary to prevent substantial mixing between the first layer material and the second layer material when the second layer material is added to the die. Subsequent to partial compression of the first layer material, the second layer material is then added to the die containing the first layer. The first and second layer materials are then compressed together to form a tablet having two layers.

Typically, the first layer material constitutes about 50% to 90% of the total weight of the final tablet. Preferably, the first layer material constitutes about 70% of the total weight of the tablet. The second layer material typically constitutes about 50% to 10% of the total weight of the final tablet. Preferably, the second layer material comprises about 30% of the total weight of the final tablet.

Since the first layer material had been previously partially compressed into a layer, substantial mixing of the second layer material with the first layer material is avoided. The two layer structure of the present invention substantially prevents contact between the pH-lowering agent and the peptide and surfactant. Specifically, at the interface between the two layers, typically less than 0.1% of the peptide contacts the pH-lowering agent.

After the tablets are removed from the press, the two-layer table cores are coated with a water-soluble coating or seal coat having a composition as described above. The coating is accomplished in a manner known in the art. As also described above, the water-soluble coating substantially prevents contact between the pH-lowering agent and the enteric coating to be applied.

After the water-soluble coating dries, the tablets are coated with an enteric coating. As described above, the enteric coating does not dissolve in acidic conditions (low pH), and therefore the enteric coating substantially prevents dissolution of the tablet in the acid conditions of the stomach, protecting the peptides in the tablet from the various proteases and digestive enzymes present in the stomach. Once the coated tablet enters the small intestine (having a higher local pH), the enteric coating dissolves. However, the inventors have found that in the absence of a separate coating positioned between the enteric coating and pH-lowering agent, the pH-lowering agent inhibits dissolution of the enteric coating because of the lower local pH induced by the pH-lowering agent. Thus, to effectively dissolve the enteric coating and prevent retardation of release of the active agents, one embodiment of the invention coats the tablets with a water-soluble coating before the enteric coating. Therefore, the enteric coating can readily dissolve without inhibition by the pH-lowering agent present in the tablet.

EXAMPLES

The following examples are representative, not limiting, of the invention.

Example 1

Table 1 provides an exemplary description of a typical embodiment of the present invention. The first layer pH-lowering agent granulation was processed using a GPCG-5 fluid bed unit, manufactured by Glatt Air Techniques, Inc. Further, the second layer peptide/surfactant granulation was processed using a GPCG-3 fluid bed unit, also by Glatt Air Techniques, Inc. The surfactant was milled prior to granulation using a commercially available Fitzmill equipped with a size 00 screen at high speed in hammers forward mode. The water was present only for processing and was evaporated out prior to compression into tablets.

Two-layer tablets were compressed using a Key BBC-4 two-layer press, commercially available from Key International, Inc., Englishtown, N.J. The citric acid blend was used as the first layer and accordingly was placed in a die of the tableting press first and then partially compressed. Next, the salmon calcitonin and surfactant granulation was added to the die after the partial compression step, and both layers were then compressed together to form the layered tablet. As a comparative example, a monolayer tablet stability study was conducted in which the peptide, surfactant, and pH-lowering agent were combined in a single layer as shown in Table 3.

To determine the relative stability of tablets manufactured from the materials described in Table 1 above, tablets having the composition set forth in the table were packaged with two 1 gram desiccant canisters in induction sealed 90 cc HDPE bottles. The results of stability testing are shown in Table 2. In Table 2, the % LC (label claim) was determined as an average value of three tablets, tested using high pressure liquid chromatography. Accordingly, the initial % LC is relative to the amount of peptide present in the dosage form, and is used only as a baseline for subsequent measurements. The "% Recovered" was calculated according to final % LC÷initial % LC*100. The % noted under "Storage Condition" is described as percent relative humidity (RH).

TABLE 1

Composition of first and second layer prototype granulations/blends

| FIRST LAYER COMPONENTS | Mg/tablet | Batch Quantity (g) | SECOND LAYER COMPONENTS | mg/tablet | Batch Quantity (g) |
|---|---|---|---|---|---|
| PH-Lowering Agent Granulation | | | Peptide/Surfactant Granulation | | |
| Povidone USP | 25.0 | 350 | Salmon Calcitonin, peptide | 0.2 | 2.00 |
| Purified Water USP | — | 1750 | Povidone USP | 11.0 | 110 |
| Citric Acid Powder | 500.0 | 7000 | Purified Water USP | — | 550 |
| Microcrystalline Cellulose | 50.0 | 700 | Lauroyl 1-carnitine, milled | 50.0 | 500 |
| | | | Microcrystalline Cellulose | 158.8 | 1588 |
| Total granulation | 575.0 | 8050 | Total granulation | 220.0 | 2200 |
| PH-Lowering Agent Final Blend | | | Peptide/Surfactant Final Blend | | |
| Microcrystalline Cellulose | 65.3 | 915 | Silicon dioxide | 2.2 | 22 |
| Talc | 6.5 | 91 | Stearic acid | 2.2 | 22 |
| Magnesium Stearate | 6.5 | 91 | | | |
| Total blend | 653.3 | 9147 | Total blend | 224.4 | 2244 |

During the application of the salmon calcitonin/binder solution to the surfactant and excipient, the size of the granules progressively enlarged. However, it was observed that these granules fractured into smaller particles during drying, resulting in a material with moderate flow properties.

The citric acid was granulated by spraying a povidone binder solution onto a fluidized bed of citric acid and microcrystalline cellulose. The resultant dried material was highly granular, essentially lump-free and free flowing. The "final blend" ingredients at the bottom of Table 1 where added to the respective granules after the initial granulation, drying, and milling, as described above.

TABLE 2

Three month recovery of salmon calcitonin (peptide) 0.2 mg two layer enteric coated tablet manufactured using a two layer press as described above.

| Stabilization Approach (General description) | Initial, % LC | Storage Condition | Final, % LC | Percent recovered |
|---|---|---|---|---|
| Layer 1: peptide/surfactant granulation. | 104.8 | 4° C. | 102.2 | 97.5 |
| | | 25° C./60% | 96.5 | 92.1 |

| Layer 2: pH-lowering agent granulation. | 30° C./60% | 93.2 | 88.9 |
| --- | --- | --- | --- |
| | 40° C./75% | 75.2 | 71.8 |

For the tablets described in Table 3, the tablets were manufactured using similar materials as set forth in Table 1, on a Manesty Beta Press. Each tablet contained about 0.2 mg of the peptide, about 500 mg. of the pH-lowering agent and about 50 mg. of the surfactant. In the last example, each tablet also contained about 100 mg. of microcrystalline cellulose. The constituents were combined in the manner described in Table 3 to form a mono-layer tablet.

TABLE 3

Evaluation of different stabilization strategies on the stability of salmon calcitonin peptide in monolayer enteric coated tablets after 3 months of storage.

| Stabilization Approach (General description) | Initial % LC | Storage Condition | Final, % LC | Percent recovered |
| --- | --- | --- | --- | --- |
| Control monolayer salmon calcitonin/lauroyl l-carnitine/citric acid granulation. | 92.2 | 4° C. 25° C./60% | 93.1 75.7 | 101.0 82.1 |
| Salmon calcitonin/citric acid granulation, pH 3.5, blended with lauroyl l-carnitine. | 88.4 | 4° C. 25° C./60% 40° C./75% | 89.8 59.7 12.4 | 101.6 67.5 14.0 |
| Salmon calcitonin/citric acid granulation blended with lauroyl l-carnitine. | 91.0 | 4° C. 25° C./60% 40° C./75% | 95.4 70.5 20.9 | 104.8 77.5 23.0 |
| Salmon calcitonin/ microcrystalline cellulose granulation blended with lauroyl l-carnitine and citric acid granulation. | 96.7 | 4° C. 25° C./60% 40° C./75% | 94.5 80.8 44.0 | 97.7 83.6 45.5 |

A comparison of the data provided in Tables 2 and 3 indicates that by separating the peptide from the pH-lowering agent in a multi-layer tablet, the shelf life of the peptide is significantly enhanced. For example, at 40° C. and 75% relative humidity, 71.8% of the peptide was recovered from the bi-layer tablets after 3 months, as shown in Table 2. However, with respect to the mono-layer tablets, at 40° C. and 75% relative humidity, depending on the stabilization method only 14%, 23% and 45% of the peptide was recovered after 3 months, as shown in Table 3.

In the next examples, a series of two layer tablets were manufactured with strengths ranging from 0.05 mg to 0.5 mg, and subjected to a battery of analyses. Table 4 shows the precise composition of salmon calcitonin 0.5 mg two layer enteric coated tablets. Although magnesium stearate is preferred, stearic acid was used in the second layer, as described in Table 4. Because the pharmaceutical active ingredient is present in such minute quantities relative to the other ingredients, all lower tablet strengths were made by dissolving a proportionally smaller quantity of salmon calcitonin in the binder solution while maintaining the quantities for the other components. A Key BBC-4 two layer rotary press was used to compress the final blends into oval-shaped plain faced two layer tablets (0.720×0.365×0.052) according to the guides listed in Table 5. Thereafter the tablet cores were sealed and enteric coated.

TABLE 4

Composition of a salmon calcitonin 0.5 mg two layer enteric coated tablet

| NO. | % w/w | INGREDIENTS | FORMULA PER 1000 TABLETS |
| --- | --- | --- | --- |
| First Layer | | | |
| 1 | 50.01 | Citric Acid, USP/EP Anhydrous Powder | 500.0 g |
| 2 | 5.00 | Microcrystalline Cellulose, NF/EP | 50.0 g |
| 3 | 2.50 | Povidone, USP/EP | 25.0 g |
| 4 | q.s. | Purified Water USP | q.s.[1] |
| 5 | 6.53 | Microcrystalline Cellulose, NF/EP | 65.3 g |
| 6 | 0.65 | Talc, UPS (400) | 6.5 g |
| 7 | 0.65 | Magnesium Stearate (Non-Bovine) | 6.5 g |
| | 65.34 | First Layer Total Weight | 653.3 g |
| Second Layer | | | |
| 8 | 0.05 | Salmon Calcitonin | 0.5 mg |
| 9 | 15.85 | Microcrystalline Cellulose, NF/EP | 158.5 g |
| 10 | 5.00 | Lauroyl-l-Carnitine HCl, milled | 50.0 g |
| 11 | 1.10 | Povidone, USP/EP | 11.0 g |
| 12 | q.s. | Purified Water USP | q.s.[1] |
| 13 | 0.46 | Croscarmellose Sodium | 4.6 g |
| 14 | 0.23 | Silicon Dioxide, Colloidal NF/EP Anhydrous | 2.3 g |
| 15 | 0.25 | Stearic Acid Powder, NF Triple Pressed | 2.3 g |
| | 88.26 | Second Layer Total Weight Tablet Core Total Weight | 229.2 g 882.5 g |
| 16 | 2.65 | Hydroxypropylmethylcellulose and polyethylene glycol (Opadry ® Clear) | 26.5 g |
| 17 | q.s | Purified Water USP/EP | q.s.[1] |
| | 90.90 | Film Coated Tablet Total Weight | 909.0 g |
| 18 | 6.99 | Polymer of Methacrylic Acid and Methacrylates (Eudragit L30D) | 69.9[2] g |
| 19 | 0.70 | Talc USP (400) | 7.0 g |
| 20 | 1.40 | Triethyl Citrate, NF | 14.0 g |
| 21 | q.s | Purified water USP/EP | q.s.[1] |
| | 100.00 | Enteric Coated Tablet Total Weight | 999.9 g |

[1]Does not appear in final product.
[2]Available as a 30% w/w aqueous dispersion; formula listed as polymer solids content.

TABLE 5

Guides employed for the compression of salmon calcitonin 0.5 mg two layer tablets

| | | Working Limits | | | Alert Limits | | |
| --- | --- | --- | --- | --- | --- | --- | --- |
| | Target | ± % | Low | High | ± % | Low | High |
| Wt. of 10 First Layer Tabs (g) | 6.53 | 5 | 6.20 | 6.86 | 8 | 6.01 | 7.05 |
| Wt. of 10 Second Layer (g) | 2.29 | 5 | 2.18 | 2.40 | 8 | 2.11 | 2.47 |
| Wt. of 10 Total Tablets (g) | 8.82 | 5 | 8.38 | 9.26 | 8 | 8.11 | 9.53 |
| Hardness (kP) | 20 | N/A | 16 | 24 | N/A | N/A | N/A |

The active pharmaceutical ingredient is incorporated into the tablet at extremely low levels and it was, therefore, anticipated that tablet content uniformity could be problematic. For this reason, during the early stages of process development, it was concluded that a top spray fluid bed process would be the best approach to homogeneously distribute the polypeptide onto the massive excipients. Table 6 displays the results of content uniformity, dissolution, and stability of salmon calcitonin 0.05, 0.1, 0.2, and 0.5 mg two layer enteric coated tablets.

of the drug could not be accounted for from the 0.5 mg tablet after six months of storage at ambient conditions. These data suggest that the room temperature storage stability is prob-

TABLE 6

Content uniformity, dissolution, and stability results of salmon calcitonin (peptide) two layer enteric coated tablets

| Peptide strength | Content Uniformity[1] | | Peptide Dissolution Profile, %[2] | Initial, % LC[4] | Stability[3] | | |
|---|---|---|---|---|---|---|---|
| | Peptide, % LC | Lauroyl 1-carnitine, % LC | | | Storage Condition | Three Months % LC | Six Months % LC |
| 0.5 mg | 102.5 RSD = 1.0 | 98.5 RSD = 0.9 | Acid stage: 0%[5] Buffer stage: 15 min.: 0 30 min.: 0 45 min.: 25 (19-43) 60 min.: 91 (61-101) 75 min.: 99 (91-103) | 103.6 | 4° C. 25° C./60% 30° C./60% 40° C./75% | 105.4 98.2 98.4 63.6 | 106.2 96.1 89.2 — |
| 0.1 mg | 108.3 RSD = 1.4 | 99.0 RSD = 1.6 | Acid stage: 0% Buffer stage: 15 min.: 0 30 min.: 2 (0-7) 45 min.: 23 (11-46) 60 min.: 71 (46-111) 75 min.: 98 (87-103) | 105.2 | 4° C. 25° C./60% 30° C./60% 40° C./75% | — — — — | — — — — |
| 0.2 mg | 99.6 RSD = 1.3 | 95.4 RSD = 1.3 | Acid stage: 0% Buffer stage: 15 min.: 0 30 min.: 5 (2-8) 45 min.: 31 (19-42) 60 min.: 79 (53-94) 75 min.: 93 (90-95) | 108.7 | 4° C. 25° C./60% 30° C./60% 40° C./75% | 105.5 102.1 97.8 68.3 | 105.6 95.0 85.2 — |
| 0.5 mg | | | Acid stage: 0% Buffer stage: 15 min.: 0 30 min.: 37 (1-84) 45 min.: 86 (82-89) 60 min.: 85 (82-87) | 101.8 | 4° C. 25° C./60% 30° C./60% 40° C./75% | 98.1 93.2 87.4 42.6 | 95.9 85.8 74.1 — |

[1] Average content uniformity and % RSD of salmon calcitonin and lauroyl 1-carnitine was determined using 10 tablets.
[2] Dissolution results show average and range of six tablets.
[3] Thirty tablets packaged with two 1 gram desiccant canisters in induction sealed 90 cc HDPE bottles. Stability results average value of three tablets.
[4] Calculated according to final % LC + initial LC.
[5] Acid stage of enteric coated tablet dissolution testing conducted for 120 minutes prior to buffer stage.
Note: All samples tested using HPLC. Stability results of the 0.05, 0.1, and 0.2 mg tablets are from different batches than those used to obtain the content uniformity and dissolution data.

Assay of the final tablets revealed that all strengths had excellent content uniformity for both the salmon calcitonin and the lauroyl l-carnitine and passed the USP criteria for content uniformity (all tablets 85%-115% of LC with RSD≦6%. It was found that nearly all of the individual test tablets were within 5% of the label claim value and that no tablet differed by more than 7% from LC. In addition, relative standard deviations of the tablets were tight, ranging from 0.9 to 1.6%. During dissolution analysis, the active pharmaceutical ingredient was not detected in the acidic media of any of the tested tablets, indicating that all tablet doses satisfied the USP dissolution requirements for enteric coated tablets. It can be seen in Table 6 that the enteric coat consistently delayed the dissolution of the salmon calcitonin for at least fifteen minutes in the buffer. Thereafter, 60-75 minutes was typically required for dissolution of greater than 75% of the drug load. Stability results of the three strengths demonstrated that greater than 90% of the initial quantity of the active pharmaceutical ingredient could be recovered after three months of storage at ambient conditions. In addition, it was found that slightly more than 15% ably between three and six months. Analysis of the samples in the refrigerator conditions for six months indicate that 5° C. would be required for the long-term storage of the salmon calcitonin tablets.

In a next example, a proof of concept clinical batch of salmon calcitonin 0.5 mg two layer enteric-coated tablets was manufactured using the formulation listed in Table 4. In this study, both the first layer and second layer granulations were prepared in a GPGC-5 fluid bed processor. The dried granulations were delumped using a Comil (Quadro Engineering, Inc., Ontario, Canada), and the granulations were separately mixed with delumped extragranular excipients in a twenty-four liter Matcon Buls bin blender. A Key BBC-4 two layer rotary press was used to compress the final blends into oval-shaped plain faced two layer tablets (0.720×0.365× 0.052), according to the guides listed in Table 5. Crushing strength was determined immediately after compression with a hardness tester. Tablet cores were seal coated and enteric coated in a 24" Accella-Cota device.

The salmon calcitonin 0.5 mg clinical batch was evaluated in a single center study employing an open label, single dose, randomized, three treatment phase crossover design (Hammersmith II trial). A total of sixteen healthy volunteers comprised of eight males and eight females received the study medication. Each subject received an oral dose of the test tablet and, on a separate occasion, one dose (0.04 mg) of an inhaled calcitonin based formulation as a positive control. The subjects were fasted from midnight preceding the day of the administration of the dosage form, but were allowed free access to water. For each of the oral phases, blood samples were collected prior to dosing and every fifteen to thirty minutes up to three hundred minutes post dosing. A washout period of seven days occurred between subsequent treatment phases. Plasma calcitonin concentration was determined by PPD Pharmoco, Richmond, Va. Analysis of the test results from the proof of concept clinical study confirmed that the prototype two layer formulation was effective in promoting the oral absorption of the salmon calcitonin polypeptide. Quantifiable levels of salmon calcitonin could be detected in the plasma of a majority (greater than 80%) of the subjects following the administration of the oral dosage form. In general, the pharmacokinetic parameters exhibited high interpatient variability. Average $C_{max}$ values of the oral tablet dose was 167±218 pg/ml with a range of 0-800. $T_{max}$ values in patients exhibiting a response range from 135-360 minutes, with an average value of 216±70 minutes. In sharp contrast, less than 19% of the patients receiving the inhaled dose had detectable blood levels.

In the next example, a pilot scale-up batch of placebo and active salmon calcitonin 0.1 mg two layer enteric coated tablets were prepared to evaluate the processability of the entire manufacturing procedure, define the processing conditions at scale, and aid in the transfer of the process to the manufacturing site. Tablets were prepared using the general formulation listed in Table 4 with 0.1 mg rather than 0.5 mg or no active pharmaceutical ingredient in the case of the placebo batch.

Both the first layer and second layer granulations were manufactured in the GPGC-60 fluid bed processor and top spray mode using the process conditions listed in Table 7.

TABLE 7

Processing conditions employed for the pilot scale manufacture of citric acid and salmon calcitonin/lauroyl l-carnitine granulations using a GPCG-60 fluid bed unit, manufactured by Glatt Air Techniques, Inc.

| FIRST LAYER (Citric Acid) GRANULATION PARAMETERS USING A GPCG-60 (Two 65 kg batches) | | SECOND LAYER (Salmon Calcitonin/lauroyl l-carnitine) GRANULATION PARAMETERS USING A GPCG-60 (One 48 kg batch) | |
|---|---|---|---|
| Inlet air temperature | 45-55° C. | Inlet air temperature | 35-55° C. |
| Product temp. (before spraying) | 25-50° C. | Product temp. (before spraying) | 25-40° C. |
| Product temp. (during spraying) | 27-40° C. | Product temp. (during spraying) | 20-30° C. |
| Product temp. (during drying) | 27-48° C. | Product temp. (during drying) | 20-40° C. |
| Exhaust temp. (during spraying) | 27-45° C. | Exhaust temp. (during spraying) | 20-35° C. |
| Atomization air (bar) | 1.8-2.2 | Atomization air (bar) | 1.8-2.2 |
| Spray rate (ml/min) | 300-500 | Spray rate (ml/min) | 200-500 |
| Fluidization air volume | Varied to maintain product fluidization | Fluidization air volume | Varied to maintain product fluidization |
| Gun: 1.5 mm nozzle, triple head, middle port | | Gun: 1.5 mm nozzle, triple head, bottom port | |

Two sublots of the citric acid granulation (65 kg each) and one lot of the salmon calcitonin/surfactant granulation (48 kg) were prepared. Each sublot of citric acid was granulated under identical conditions by spraying a povidone binder solution onto a fluidized bed of citric acid and microcrystalline cellulose, then dried to less than 1% w/w moisture content. The citric acid granulations were highly granular, essentially lump-free, and free flowing. The salmon calcitonin/surfactant granulation was prepared by applying a solution of povidone and salmon calcitonin onto a bed of microcrystalline cellulose and lauroyl l-carnitine, and then the granulation was dried in the chamber to less than 2.5% w/w moisture content. The resultant preparation was found to be a fine material with moderate flow properties. The particle size distribution densities of the three granulations are tabulated in Table 8.

TABLE 8

Particle size distributions and densities of first and second layer granulations manufactured using a pilot scale GPCG-60.

| | Screen Size | | | | | | |
|---|---|---|---|---|---|---|---|
| | 20 | 40 | 60 | 80 | 100 | 140 | PAN |
| First Layer granulation: | | | | | | | |
| (CA) | | | | | | | |
| Weight % retained, Sublot 1 | 0.7 | 14.1 | 54.1 | 20.8 | 3.6 | 4.4 | 2.1 |
| Weight % retained, Sublot 2 | 1.9 | 9.8 | 38.3 | 20.7 | 6.1 | 9.1 | 14.0 |
| Density Sublot 1: Loose - 0.43; Tapped - 0.60 | | | | | | | |
| Density Sublot 2: Loose - 0.47; Tapped - 0.60 | | | | | | | |
| Second Layer granulation: | | | | | | | |
| (salmon calcitonin/lauroyl l-carnitine) | | | | | | | |
| Weight % retained | 1.6 | 1.7 | 1.4 | 2.9 | 2.9 | 9.5 | 80.0 |
| Density; Loose - 0.40; Tapped - 0.60 | | | | | | | |

All dried granulations were passed through a Comil (Quadro Engineering, Inc., Ontario, Canada) set at 500 RPM and equipped with a size 2F094R037/41 screen. Both citric acid granulations were blended together for 5 minutes at 15 RPM in a single step along with the delumped extragranular excipients in a 500 L Matcon Buls Bin blender. The salmon calcitonin/surfactant granulation was mixed with delumped silicon dioxide and croscarmellose sodium for 5 minutes at 15 RPM in a 250 L Matcon Buls Bin blender. Thereafter, the stearic acid lubricant was added to the mixture and blending continued for an additional 3 minutes. All blends flowed smoothly from the bins during discharge in their entirety.

A Key BBC-4 two layer rotary press was used to compress the final blends into oval-shaped, plain faced, two layer tablets (0.720×0.356×0.052) according to the guide listed in Table 5. The press was completely tooled with 35 stations and run at 18 RPM. Crushing strength was determined immediately after compression with a hardness tester. Individual layer weights remained consistent throughout the entire compression operation. No signs of any sticking problems were evident after prolonged compression of the two layer formulations.

Friability analysis of the tablet cores demonstrated that the tablets were highly resistant to chipping and/or fracture into the two separate layers (0.01% friability after four minutes of tumbling). Tablet cores were subsequently seal coated and enteric coated in a 48" Accela-Cota. The final enteric coated tablets were visually acceptable.

All tested tablet cores were seal coated using a hydroxypropylmethylcellulose coating system applied at a coverage level of 3% w/w followed by enteric coating with an Eudragit L30D-based (a methacrylic and methacrylate polymer) enteric coating dispersion containing 100 parts solid polymer, 20 parts triethyl citrate, and 10 parts talc (total 20% w/w solids content) applied at a target coverage level of 10% w/w. Coating operations were accomplished using a Freund Hi-Coater Model HCT-30, Vector Corp., Marion, IA USA (<1 kg cores) or a 24" Accela-Cota, Thomas Engineering, Inc., Hoffman Estates, IL, IA USA (>6 kg cores), or a 48" Accela-Cota (>90 kg cores) depending on the amount of tablet cores to be coated.

Although illustrated and described herein with reference to certain specific embodiments and examples, the present invention is nevertheless not intended to be limited to the details shown. Rather, the claims should be read to include various modifications within the scope and range of equivalents of the claims, without departing from the spirit of the invention.

What is claimed is:

1. A method of making a dosage form for oral delivery of a peptide comprising the steps of:
    granulating a pH-lowering agent to form a first layer material;
    combining a peptide and at least one absorption enhancer to form a second layer material;
    adding said first layer material to a die and compressing said first layer material to create a first layer such that substantial mixing between the first layer material and the second layer material is prevented when the second layer material is added to the die;
    adding said second layer material to said die;
    compressing said first and said second layer materials together to form a lamination consisting of two layers wherein said first and said second layers interface with one another but wherein, at said interface, less than about 0.1% of the peptide contacts the pH-lowering agent to prevent substantial mixing between the first layer material and the second layer material to avoid interaction in the lamination between the pH-lowering agent and the peptide;
    coating said lamination with a water-soluble coating to form a coated lamination; and
    applying an enteric coating over said coated lamination to form a tablet, wherein said water-soluble coating substantially prevents said first layer material from contacting said enteric coating.

2. The method of claim 1, wherein said first layer material is partially compressed before said second layer material is added to said die.

3. The method of claim 1, wherein the combining step further comprises combining an excipient with said peptide and said absorption enhancer.

4. The method of claim 3, wherein said excipient comprises microcrystalline cellulose.

5. A pharmaceutical composition for oral delivery of a peptide, said pharmaceutical composition comprising the dosage from prepared according to the method of claim 1, wherein said pharmaceutical composition comprises:
    a lamination consisting of a first layer of compressed material comprising at least one pharmaceutically acceptable pH-lowering agent and a second layer comprising a therapeutically effective amount of a peptide, said lamination further comprising an interface between said first and said second layers;
    at least one absorption enhancer effective to promote bioavailability of said peptide; and
    an enteric coating surrounding said lamination,
    wherein, at said interface, less than about 0.1% of the peptide is in contact with the pH-lowering agent, which prevents substantial mixing between the first layer material and the second layer material to avoid interaction in the lamination between the pH-lowering agent and the peptide.

6. The pharmaceutical composition of claim 5, wherein said second layer further comprises said absorption enhancer.

7. The pharmaceutical composition of claim 5, wherein said composition further comprises a water-soluble coating surrounding said lamination and positioned between said lamination and said enteric coating.

8. The pharmaceutical composition of claim 5, wherein said enteric coating is present at a weight which is no more than 20% of the weight of the remainder of said composition excluding said enteric coating.

9. The pharmaceutical composition of claim 5, wherein said enteric coating is present at a weight which is between 5-55% of the weight of the remainder of said composition excluding said enteric coating.

10. The pharmaceutical composition of claim 5, wherein said absorption enhancer is a surface active agent.

11. The pharmaceutical composition of claim 2, wherein said surface active agent is absorbable or biodegradable.

12. The pharmaceutical composition of claim 2, wherein said surface active agent is selected from the group consisting of acyl carnitines, phospholipids, and bile acids.

13. The pharmaceutical composition of claim 2, wherein said surface active agent comprises lauroyl l-carnitine.

14. The pharmaceutical composition of claim 5, wherein said peptide comprises salmon calcitonin.

15. The pharmaceutical composition of claim 14, wherein said pH-lowering agent is added in a quantity sufficient to lower the pH of 10 milliliters of a 0.1 M aqueous sodium bicarbonate solution to less than or equal to 5.5.

16. The pharmaceutical composition of claim 5, further comprising an excipient.

17. The pharmaceutical composition of claim 16, wherein said excipient comprises microcrystalline cellulose.

18. The pharmaceutical composition of claim 5, wherein said pH lowering agent comprises citric acid.

19. A method for enhancing the bioavailability of a peptide delivered orally, said method comprising selectively releasing said peptide, together with at least one pH-lowering agent and at least one absorption enhancer, into a patient's intestine following passage of said peptide, pH-lowering agent and absorption enhancer through said patient's mouth and stomach under protection of an enteric coating and a water soluble coating, wherein:
said enteric coating substantially prevents contact between stomach proteases and said peptide;
said water-soluble coating substantially prevents contact between said pH-lowering agent and said enteric coating; and
said peptide and said pH-lowering agent are contained in separate layers of the laminate prepared according to the method of claim 1 that interface with one another and, at said interface, less than about 0.1% of the peptide contacts the pH-lowering agent to prevent substantial mixing between the peptide and the pH-lowering agent to avoid interaction therein between the pH-lowering agent and the peptide.

20. The method of claim 19, wherein said pH-lowering agent is present in said pharmaceutical composition in a quantity sufficient to lower the pH of 10 milliliters of a 0.1 M aqueous sodium bicarbonate solution to less than or equal to 5.5.

21. A tableted dosage form for oral delivery of a peptide prepared according to the method of claim 1, wherein said dosage form comprises:
a lamination consisting of a first layer of compressed material comprising at least one pharmaceutically acceptable pH-lowering agent and a second layer comprising a therapeutically effective amount of a peptide, said lamination further comprising an interface between said first and said second layers;
at least one absorption enhancer effective to promote bioavailability of said peptide;
a water-soluble coating formed over said lamination; and
an enteric coating formed over said water-soluble coating, wherein said water-soluble coating substantially prevents contact between said pH-lowering agent and said enteric coating,
wherein, at said interface, less than about 0.1% of the peptide contacts the pH-lowering agent to prevent substantial mixing between the first layer material and the second layer material to avoid interaction in the lamination between the pH-lowering agent and the peptide.

22. The dosage form of claim 21, wherein said peptide comprises salmon calcitonin.

23. The dosage form of claim 22, wherein said pH-lowering agent is present in a quantity sufficient to lower the pH of 10 milliliters of a 0.1 M aqueous sodium bicarbonate solution to less than or equal to 5.5.

24. The dosage form of claim 21, wherein said pH-lowering agent comprises citric acid.

25. The dosage form of claim 21, wherein said absorption enhancer comprises lauroyl l-carnitine.

26. The dosage form of claim 21, wherein said water-soluble coating comprises hydroxypropylmethylcellulose.

27. The dosage form of claim 21, wherein said enteric coating comprises a polymer of methacrylic acid and methacrylate.

28. The dosage form of claim 21, wherein said first layer further comprises a disintegrant.

29. The dosage form of claim 21, wherein said disintegrant comprises croscarmellose sodium.

30. The dosage form of claim 21, wherein:
said peptide comprises salmon calcitonin;
said pH-lowering agent comprises citric acid present in a quantity sufficient to lower the pH of 10 milliliters of a 0.1 M aqueous sodium bicarbonate solution to less than or equal to 5.5;
said absorption enhancer comprises lauroyl l-carnitine;
said water-soluble coating comprises hydroxypropylmethylcellulose;
said enteric coating comprises a polymer of methacrylic acid and methacrylate; and
said second layer further comprises croscarmellose sodium.

* * * * *